(12) United States Patent
Cheng

(10) Patent No.: US 6,485,512 B1
(45) Date of Patent: Nov. 26, 2002

(54) TWO-STAGE LIGHT CURABLE STENT AND DELIVERY SYSTEM

(75) Inventor: E Tina Cheng, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 210 days.

(21) Appl. No.: 09/671,664

(22) Filed: Sep. 27, 2000

(51) Int. Cl.[7] .................................................. A61F 2/06
(52) U.S. Cl. ..................... 623/1.21; 623/1.45; 606/194; 606/198
(58) Field of Search ................................. 606/191, 192, 606/194, 195; 623/23.69, 1.1, 1.15, 1.32, 1.38, 1.44–1.48, 1.21, 11, 12

(56) References Cited

U.S. PATENT DOCUMENTS

| | | | |
|---|---|---|---|
| 3,866,599 A | | 2/1975 | Johnson |
| 4,355,426 A | * | 10/1982 | MacGregor ................. 623/1.32 |
| 5,059,211 A | * | 10/1991 | Stack et al. .................. 606/154 |
| 5,334,201 A | | 8/1994 | Cowan |
| 5,344,444 A | | 9/1994 | Glastra |
| 5,723,004 A | * | 3/1998 | Dereume et al. ........... 623/1.35 |
| 5,766,204 A | | 6/1998 | Porter et al. |
| 5,891,082 A | | 4/1999 | Leone et al. |
| 5,997,570 A | | 12/1999 | Ligtenberg et al. |
| 6,013,714 A | | 1/2000 | Haruta et al. |
| 6,017,973 A | | 1/2000 | Tamura et al. |
| 6,027,779 A | * | 2/2000 | Campbell et al. ........... 428/35.8 |
| 6,174,326 B1 | | 1/2001 | Kitaoka et al. |

OTHER PUBLICATIONS

*Clinical Forum*, U.S. Department of Labor; Manufacturer: Chameleon Dental Products, Inc; Prepared: Oct. 24, 1985.

* cited by examiner

Primary Examiner—David J. Isabella
Assistant Examiner—Urmi Chattopadhyay
(74) Attorney, Agent, or Firm—Fulwider Patton Lee & Utecht, LLP

(57) ABSTRACT

An expandable stent including a light and water curable resin embedded in a stent wall wherein the wall is formed to be transmissive to light for curing the resin and transmissive to fluid for further curing of the resin. A catheter delivery system may be provided for in vivo delivery, expansion, rigidization, and installation of the stent into a body lumen.

7 Claims, 2 Drawing Sheets

TWO-STAGE LIGHT CURABLE STENT AND DELIVERY SYSTEM

BACKGROUND OF THE INVENTION

This invention relates to devices for the treatment of heart disease and particularly to endo arterial prosthesis, which are commonly called stents. More particularly, the invention relates to improved light curable stents and improved catheter assemblies to facilitate the insertion and implantation of light curable stents in a body lumen.

A focus of recent development work in the treatment of heart disease has been directed to endo-prosthetic devices called stents. Stents are generally tube shaped intravascular devices which are placed within a blood vessel to structurally hold it open. The device can be used to prevent restenosis and to maintain the patency of a blood vessel immediately after intravascular treatments.

Stents often require extreme flexibility so as to be capable of being transported through varying and tortuous turns and diameters of the vessel pathway prior to arriving at the desired stenotic site. Expandable stents are so designed. Typically, expandable stents are delivered in a collapsed form to the stenotic region, expanded from within by a dilation balloon, and the ability to remain expanded so as to continue holding open the vessel after the balloon has been withdrawn.

Many expandable stents, however, do not retain a fully expanded state after the balloon has been withdrawn. Many such stents have been known to recoil after the inflation procedure due to elastic properties of the stent and applied stenotic pressure. If the recoil is great enough, the stent may also, due to lack of frictional resistence holding it in place, become dislodged from its location, and migrate downstream. On such occasions, adequate lumenal flow can therefore be jeopardized. As a result, another procedure is needed to address a stent opening that has been so reduced.

Additionally, an expandable stent with plastic properties may be severely limited as to the degree of expandability of the stent from a deformed state into a permanently expanded configuration. It is therefore desirable for an expandable stent not to be so limited by its plastic properties and instead rely on different means for support when expanded beyond its ability to retain a plastically expanded shape.

There have been efforts to address the need to rigidize a stent after delivery and expansion. Some efforts have included, for example, the deposition of transformable materials in a stent wall. The mixing of epoxy components, for example, inside the wall of a stent has been heretofore disclosed. U.S. Pat. No. 5,344,444 (Glastra), discloses a stent wall formed with breakable internal partitions separating mixable epoxy components. The stent is designed to be delivered in a non-expanded state, and is thereafter subject to expansion by the dilation balloon.

According to Glastra, the expansion of the stent breaks open the partition walls allowing the epoxy components to mix, thereby hardening the resulting composition. Such stents, however, suffer the shortcoming that performance is dependant upon satisfactory formation and breaking of the partitions and the adequate intermixing of the epoxy components after the partitions have broken down.

Glastra also discloses a stent with premixed epoxy enclosed in the stent wall. However, the pre-mixing stage takes place prior to insertion of the stent into the lumenal cavity and therefore requires the stent to not only be dispatched rapidly to the lumenal site, but also expanded before the mixed epoxy hardens.

Similarly, U.S. Pat. No. 5,334,201 (Cowan), discloses epoxy filled stent walls where epoxy components are partially cured prior to insertion into the body lumen. Once again, the performance of the stent is dependant on the time limitation for in vivo delivery, expansion, and rigidization of stent prior to hardening of the epoxy. If hardened too soon, the stent becomes more difficult if not impossible to deliver to the lumenal location. Should the stent reach the intended location prior to curing, expansion of the stent must take place rapidly and prior to setting of the epoxy.

Cowan also discloses the use of light curable materials such as epoxies and urethanes. However, Cowan also suggests that such materials are toxic to the body and therefore pose a health hazard prior to curing. To reduce the possibility of exposure to the body of the toxic materials, Cowan also discloses a biocompatable coating to isolate the toxic materials from contact with the body lumen. The enclosure of the toxic material, however, continues to pose the risk of toxic exposure should the material not be fully cured or by mere puncture, tearing, or improper manufacturing of the stent wall.

U.S. Pat. No. 5,766,204 (Porter et al.), suggests a stent made of fibers containing light curable material. Like Cowan, Porter also discloses that the light curable material be encapsulated in a fiber, and for increased toxicity protection, be encapsulated by a biocompatable material prior to curing. Porter suggests that the encapsulating material be biodegradable. Such a device while having certain utility, suffers from the shortcoming that the fiber construction is expensive to manufacture and, once degraded may for form interstitial gaps which may provide for intrusion of stenotic material. Additionally, like Cowan, the toxic curable material poses risk of exposure by the mere puncture, tearing, or improper manufacturing of the stent wall or incomplete curing of the material therein.

There has long existed a need for a stent which can be fully collapsed for deployment to the site of the stenosis and may be then expanded into position and efficiently and more safely be rigidized at that point. The present invention satisfies this need.

Expandable light curable stents require means for deployment and expansion. Stent delivery systems have evolved from angioplasty procedures. In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium. A guide wire is positioned within an inner lumen of a dilatation catheter and then both are advanced through the guiding catheter to the distal end thereof. The guide wire is first advanced out of the distal end of the guiding catheter into the patient's coronary vasculature until the distal end of the guide wire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion.

Once in position across the lesion, the balloon, which is made of relatively inelastic materials, is inflated to a predetermined size with radiopaque inflation fluid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guide wires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,451,233 (Yock); U.S. Pat. No. 5,458,651 (Klemm, et al.); and U.S. Pat. No. 5,507,768 (Lau, et al.) which are hereby incorporated herein in their entirety by reference thereto.

One problem characteristic of balloon angioplasty procedures is the large number of patients which are subject to restenosis in the treated artery. In the case of restenosis, the treated artery may again be subjected to balloon angioplasty or to other treatments such as by-pass surgery or stent insertion, if additional balloon angioplasty procedures are not warranted.

One method and system developed for delivering stents to desired locations within the patient's body lumen involves attaching a stent about an expandable member, such as a balloon on the distal end of a catheter, advancing the catheter through the patient's vascular system until the stent is in the desired location within a blood vessel, and then inflating the balloon to expand the stent within the blood vessel. The expandable member is then deflated and the catheter withdrawn, leaving the expanded stent within the blood vessel, holding open the passageway thereof.

In the event a light curable stent is deployed, application of light is needed to rigidize the stent prior to deflation and withdrawal of the balloon. Some means and methods to cure light curable stents can be found in U.S. Pat. No. 5,344,444 (Glastra); U.S. Pat. No. 5,997,570 (Ligtenberg); and U.S. Pat. No. 5,891,082 (Leone et al.).

It is desirable, however, that an apparatus used to cure light curable stents in vivo not be limited to providing multidirectional light and employing a light transmissible expansion balloon and light transmissible inflation fluid, and, alternatively not be limited to curing from within the expansion balloon. The present invention satisfies these needs.

SUMMARY OF THE INVENTION

The invention is directed to an improved stent that is deliverable in an extremely flexible state to a lumenal site and, thereafter, is expanded and transformed in vivo to a relatively more rigid state. This invention is also directed to a catheter delivery system for in vivo delivery, expansion, rigidization, and installation of expandable light curable stents into a body lumen.

The improved stent is formed to be collapsible to a low profile for ease of delivery to the lumenal site and expandable where, after delivery, it is expanded into the vessel wall. The stent is formed with a wall containing a fluid resin that is cured in two stages: first by application of light and, second, by absorption of and reaction with water. Additionally, the stent wall acts as a window for transmission of curing light to the encapsulated resin, and as a porous membrane for absorption of curing fluid for second stage hardening.

Transformation of the stent, from a flexible to a relatively rigid state, is provided by the curing, in vivo, of the photo curable resin while the stent is in an expanded state. The second stage hardening, provided by the reaction of water with the light cured resin, improves support to the stent wall and thereby its capacity to hold open the vessel. A typical lumenal environment provides adequate water for second stage curing of the encapsulated resin, the water pathway being provided to the resin by the water permeable stent wall.

In some embodiments, the stent wall chamber is small to hold only a dot of resin in a pocket, for example, and in others is essentially a tubular void to hold resin distributed thereabout to form a tubular shell. The size of the chamber and amount of resin applied is dependant on the amount and location of post-expansion wall support desired. Resin can be selectively placed where support is most needed leaving the remainder of the stent wall flexible if desired. Resin disclosed by the present invention can also be applied as a composite paste, obviating any requirement for mixing composite components inside the stent.

Before curing is started, the stent wall, including its encapsulated fluid resin, is flexible and is collapsible for ease of transport to the desired location in the vessel. The wall material possesses expandable properties to provide for expansion of the stent at the lumenal site. The wall material is also transmissive to light from at least one side, so as to facilitate exposure of the encapsulated resin fluid to application of curing light and is transmissible to water from at least one side, so as to facilitate exposure to, absorption by, and reaction with, the partially cured encapsulated resin. Once the improved stent is configured, a delivery system is needed to facilitate its delivery, expansion, rigidization, and insertion.

The improved stent is delivered to the lumenal site, expanded by the dilation balloon to engage the vessel wall, and curing light is applied hardening the resin. The light cured resin provides some support to the stent wall. The light cured resin is thereafter exposed to water from the wet lumenal environment via the permeable stent wall. The light cured resin thereafter reacts with the water thereby promoting further hardening. Once the resin has sufficiently hardened, the balloon is deflated and the catheter withdrawn leaving the hardened stent in place in the body lumen.

Stent delivery systems are typically composed of a catheter assembly encompassed at its distal end by an expandable member such as an inflatable dilation balloon. The stent is positioned about the expandable member so that the two can be transported to the lumenal site and thereafter be expanded together. Prior to deflation of the balloon, the light curable resin contained in the stent requires exposure to light to harden. The improved catheter assembly of the present invention includes a light curing apparatus for in vivo light curing of the resin. The apparatus includes at least one light emitter to be configured to project light toward the resin.

The invention can be used with the known configurations of stent delivery systems including, for example, over-the-wire (OTW) intravascular catheters and rapid exchange (Rx) intravascular catheters.

Other features and advantages of the invention will become apparent from the following detailed description, taken in conjunction with the accompanying drawings, which illustrate, by way of example, the features of the invention.

DETAILED DESCRIPTION OF PREFERRED EMBODIMENTS

Expandable stents are well known to those in the art. There exists a wide variety of configurations for implanting in human vessels. Some stents are delivered in a compressed form and self expand upon removal of a compression sheath. Others are known to expand plastically after expansion by a dilation balloon. Still others have been known to expand elastically by force from a dilation balloon and thereafter assume an expanded configuration by transformation of materials inside the stent. The subject of the present invention is directed to this latter stent technology.

The present invention discloses and includes an expandable stent that encapsulates a light curable resin in its wall, that when exposed to light, transforms the resin to a hardened state. The resin is further hardened by exposure to body fluids that enter through the sieve-like stent wall.

The enclosed resin in the stent wall is in a fluid state when introduced into the body cavity. The fluid state of the resin enhances flexibility of the tube-shaped stent so that it may travel on the end of a catheter through the varying turns and diameters of a vessel pathway toward its final destination; the site selected where flow either has been or is in danger of being restricted. Once the stent has arrived at the stenotic site, it is then expanded outwardly to meet and support the vessel wall by an inflatable balloon placed inside the tubular stent cavity.

The expanded stent needs to be rigidized so that it does not retract when the balloon is deflated and so that it can remain in its expanded condition to hold open the vessel wall. Partial rigidization is accomplished by shining a light from inside the stent onto the light curable resin contained in the expanded stent wall. The inside wall of the stent is transmissible to light like a window so that the resin can be exposed to the light and harden. The stent wall is not only transmissible to light, it also is porous like a sieve to water in the wet vessel environment. After exposure to light, the resin absorbs and reacts with water that penetrates the stent wall and more fully hardens further rigidizing the resin and thereby the stent wall. When the expanded stent wall has become sufficiently rigid and self-supporting, the balloon is deflated and withdrawn leaving behind the rigidized stent holding open the vessel.

Figure 1:
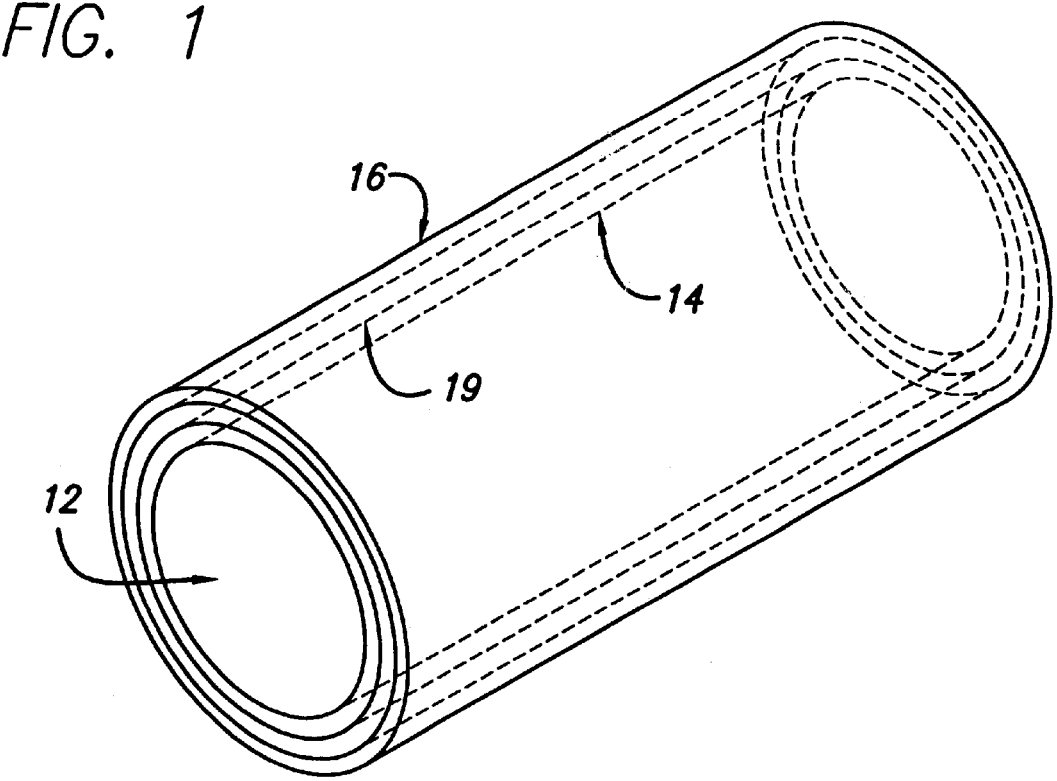
FIG. 1 is a side view of a stent embodying the present invention.
Figure 2:
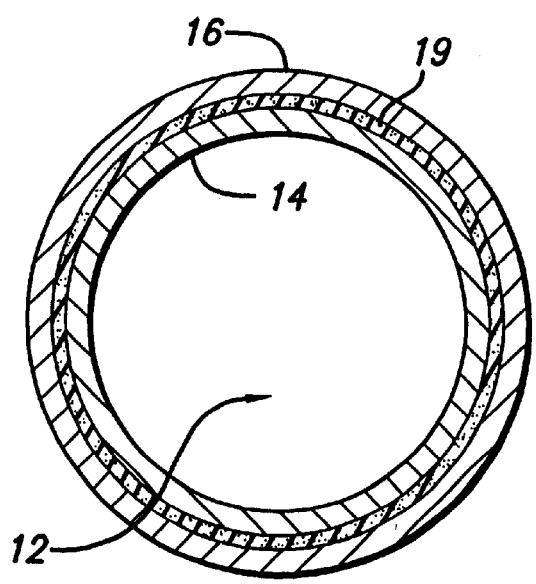
FIG. 2 is an enlarged scale of a transverse cross sectional view of the stent shown in FIG. 1.
Figure 3:
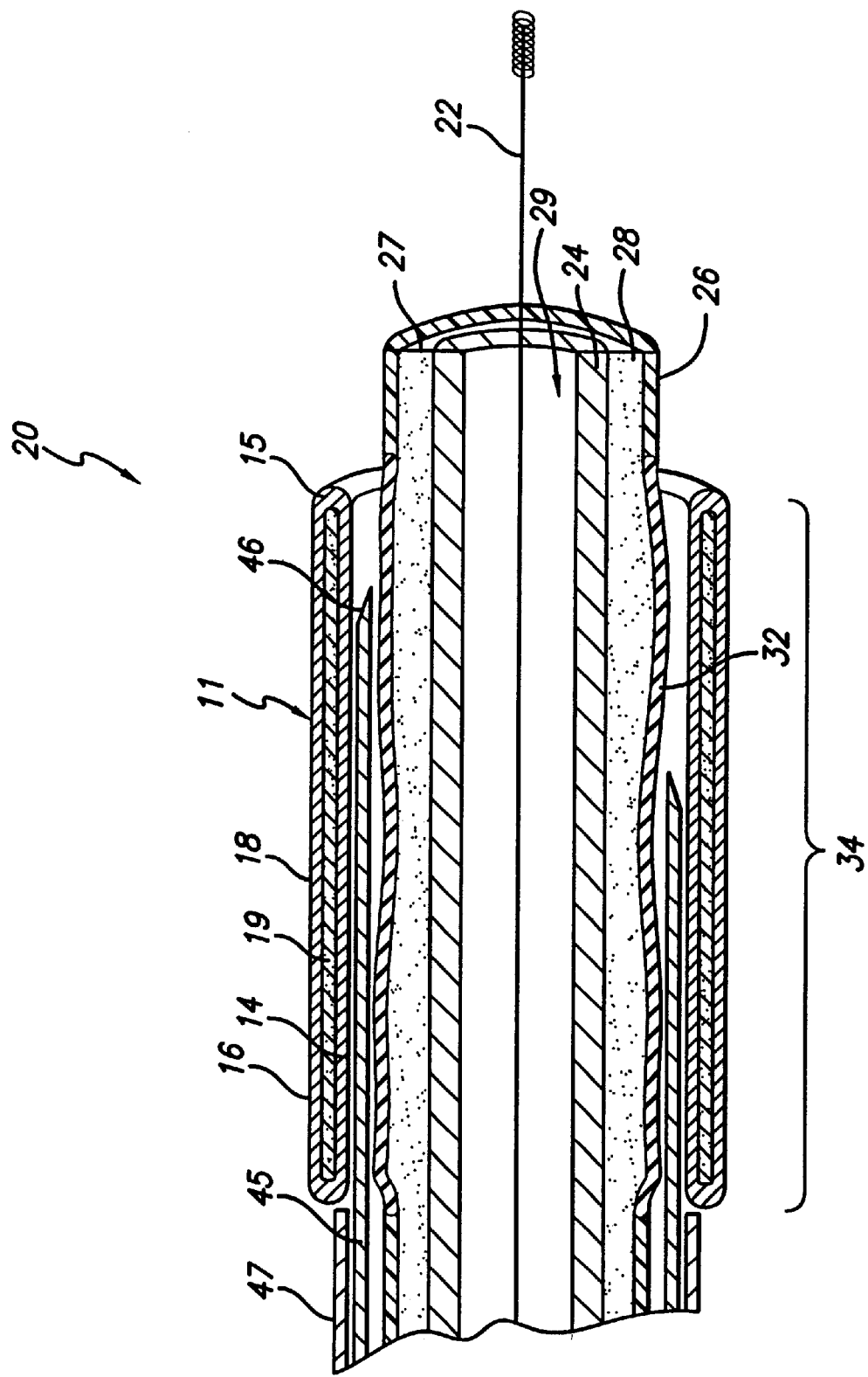
FIG. 3 is a longitudinal sectional view in reduced scale of the distal portion of a catheter assembly for deploying the stent shown in FIGS. 1 and 2.

Referring to FIGS. 1–3, the stent of the present invention includes, generally, a tubular, dual wall, highly flexible stent body 11 with a passage 12 therethrough having generally concentric inner and outer walls 14 and 16 having formed therebetween a generally annular chamber 18 which receives fluidized or highly pliable light curable resin 19. The resin 19 is selected to be responsive to selected wavelengths of light to initiate curing and to be responsive to body fluids to achieve a final stage of curing. The inner walls 14 may be constructed from any of a variety of polymers and is preferably constructed of a polymer which is transmissive to ultraviolet light to act as a window exposing the resin 19 to light energy applied to the interior of such stent. One or both of the walls 14 and 16 are constructed of a polymer which is sufficiently porous to act as a sieve to provide for flow of body fluids to penetrate there through so as to expose such resin to those fluids to facilitate curing thereof. Further details of such materials and the methods to produce fluid permeable stent walls are described in U.S. Pat. No. 4,355,426 (MacGregor); U.S. Pat. No. 5,059,211 (Stack, et al.); U.S. Pat. No. 5,723,004 (Derume, et al.); and U.S. Pat. No. 6,027,779 (Campbell, et al.), which are hereby incorporated herein in their entirety by reference hereto.

The precise placement of stents in various body lumens typically requires the delivery system to navigate the stents in a collapsed low profile condition through tortuous vessels and alike to the stenotic site where the stent is expanded to its expanded condition. It is desirable that such stents be collapsible to a very low profile condition for such navigation so as to provide minimum resistance to advancement through tight turns and narrow lumens. Then, when the stent is expanded at the stenosis site, it is desirable that it assume a relatively rigid condition to assure continued support of the vessel. Consequently, it is important that any resin relied on to maintain the rigidized configuration be curable to a high state of rigidity. Additionally, it is important to reduce potential for introduction of toxic materials into the body lumen. Moreover, it is important that the curing process be relatively rapid to, thus, minimize the time required for completion of the procedure.

It will be appreciated to those skilled in the art that the stent 11 of the present invention may take many different forms. In the preferred embodiment, such stent, in its expanded condition, is generally cylindrically shaped. Hence, the stent itself may be constructed of the concentric walls 14 and 16 which may be formed by sandwiching separate layers of polymers together leaving the chamber 18 un-adhered throughout the length of the stent except for at the ends of stent body or, if desirable, adhered at various locations along the stent body to form multiple chambers of different circumferential or longitudinal configurations.

In one embodiment, the stent is constructed by assembling separate layers of Teflon® and Silastic rubber polymer in a flat sheet and cutting the sheet with a laser. The premixed light curable resin 19 may be sandwiched between the sheets and, after or during cutting thereof, the peripheries of such sheets bonded together by a bond 15 to encapsulate the resin therein and form the generally tubular shape.

Technological advances in the dental industry have led to the development of polymer compounds that are of reduced toxicity. A resin, such as Dyract™ by Dentsply Research & Development Corporation, is a suitable example of a non-toxic resin. Such a compound is used inside the oral cavity for restoration of teeth. Dyract™, for example, requires the use of light to initially set the compound while mounted on the patient's tooth. However, Dyract™, also requires a second stage curing process that requires introduction of water after light has been applied to complete the hardening process. In dental applications, water for second stage curing is supplied by the fluids contained in the wet oral environment.

Dyract™ is a light curable polymer composite that is formed by the combining of polymerisable molecules of urethane dimethacrylate together with a resin formed from the reaction product of butane tetracarboxylic acid and hydroxyethyl methacrylate. This combination is known as a copomer. Filler particles, such as powdered glass, may be added forming a pre-mixed single paste that can be encapsulated into a stent wall without further mixing.

Upon activation by light, the polymerisable molecules of urethane dimethacrylate and the resin become interconnected into a three dimensional network that encloses the filler particles within the polymer matrix. The second stage of the curing reaction occurs as the polymerized bulk of material begins to absorb water.

After light has been applied, water molecules are absorbed by and react with the light hardened composite. During this secondary curing of the resin, the carboxyl groups of the resin dissociate and ions diffuse out from the glass surface to react within the matrix. An acidic reaction occurs between the carboxyl groups and the liberated metal cations eventually generating hydrogels within the resin structure of the copomer and resulting in further hardening of the composite. As acid decomposition of the glass occurs, fluoride is also released.

In the present invention, a light and water curable composite resin is premixed and deposited into the biocompatable stent wall. The stent is inserted into the body lumen, positioned at the site of stenosis, and expanded. Light is then applied partially hardening the composite. The encapsulated resin then gains access to water from the wet lumenal environment through the pathway provided by the permeable stent wall. The stent wall is further rigidized rapidly thereby providing additional support to the stent and to the vessel wall held open by it.

While allowing the admission of ultraviolet and visible wavelengths, many light curable resins can be formed to render the resin opaque to radio frequencies. Such radio-opaqueness may be desirable to enhance radio-detectability of the stent during, and long after, the stent insertion procedure.

Additionally, biodegradeable stent walls may be employed in resin filled stents of the present invention that contain sufficient resin that, once hardened, possesses desired structure and smoothness without the need for further presence of encapsulating stent walls.

Referring to FIG. 3, a delivery system, generally designated 20, can be utilized to deploy the stent 11. The delivery system may be in a form of a conventional balloon delivery catheter incorporating an elongated coaxial catheter system having a guidewire 22 disposed within a guidewire passage 29. An outer tubular member 26 is formed with a distal portion defining balloon 32. Housed in concentric relationship in the outer member 26 is an inner member, generally designated 24. Between outer member 26 and inner member 24 is a cavity 28 for the transport and containment of inflation fluid injectable into and withdrawable from an external source of inflation fluid. Cavity 28 is sealably terminated at the distal end of the catheter assembly by end wall 27.

The area about balloon 32 is referred to generally as the stent mounting region 34. A plurality of optic fibers 45 are mounted on the balloon in a circumferential relationship and are carried to the mounting region 34 within an exterior light transparent jacket 47. Such optic fibers 45 are of different lengths at longitudinally spacial locations and the distal ends are arranged about in a cylindrical pattern to terminate in light exchange relationship with inside the wall 14 of the stent 11. The stent is mounted about the optic fibers 45 and within the stent mounting region 34.

In one embodiment, fibers 45 are formed at their distal extremities with diagonal cuts 46 facing radially outwardly so as to act as illuminators directing light projected there through radially outwardly to illuminate the interior wall 14 of the stent 11 (FIG. 3). In this embodiment, the jacket 47 terminates proximally of the stent 11 so as to aid in positioning the stent 11 on the balloon 32 and to reduce the buildup of structure inside the stent 11 and therefore provide for a smaller stent insertion profile.

In other embodiments, the jacket 27 may be entirely removed to free the light fibers 45 from encountering the jacket. Alternatively, the jacket may extend distally about the light fibers and within the stent if positioning of the light fibers or diagonal ends 46 becomes more important. In the event the jacket is extended inside the stent, the jacket should be capable of expansion so as to enable the transfer of expansion forces from the balloon through the jacket and to the stent. In the extended jacket configuration, the jacket should also be light transmissible so that light emitted from the diagonal ends positioned inside the stent may be transmitted through the jacket reach the inner stent wall 14. Methods and materials needed to fashion an expandable light transmissible jacket are known those in the art.

To reduce unnecessary energy use and heat buildup inside the stent 11 during light emission, the diagonal ends 46 may be positioned to illuminate selectively only those portions of the stent where curing light is desired.

In other embodiments of the present invention, the light fibers 45 may be placed inside the balloon 32. The light fibers may be disposed circumferentially and longitudinally about or inside the inner member 24, with diagonal end light illuminators 46 disposed therein in staggered fashion to project light radially toward the inner stent wall 14. This embodiment provides for a reduced insertion profile of the stent 11 by eliminating the light fibers about the balloon, but also requires the dilation balloon and the inflation fluid to be transmissive to light. Additionally, an external light controller may be used to select duration and intensity of light desired in any of the embodiments that employ at least one light fiber.

In operation, it will be appreciated the stent 11 of the present invention may be manufactured from the sandwich construction as discussed above to provide a highly flexible stent body wall made up of essentially concentric tubes 14 and 16 maintaining the resin 19 distributed there about in a relatively uniform tubular configuration (FIGS. 1 and 2). If desired, various seams and partitions may be established between the tubes 14 and 16 to maintain the desired distribution of such resin 19. Additionally, such seams and partitions may be configured to form chambers defining essentially circumferential ribs of resin, longitudinal beams of resin, or even a network of crosshatches and struts such that, upon curing thereof, the circumferential ribs, longitudinal beams, or struts will provide the desired structural integrity to maintain the stent in its distended configuration.

It will be appreciated that in preparation for deployment, the balloon 32 will be deflated to a reduced diameter dictated in the present embodiment (FIG. 3) to accommodate the light fibers 45 and the stent 11 and subject to the restrictions presented by the lumenal opening and pathway to the stenosis as is known to those in the art. The flexible body wall of the stent may be expanded to be manipulated telescopically over the deflated balloon 32 into the position shown in FIG. 3 concentric about the balloon and maintained in its collapsed position. Such stent may be removably attached to such balloon by an attachment means familiar to those skilled in the art to hold such collapsed stent in position for introduction the patient's vascular system.

In the case of a coronary stent, access may be gained to the vasculature, as in the groin area of the patient, and the guide wire 22 is advanced through the vasculature to, for instance, the stenosis in the coronary artery in a manner known to those skilled in the art. The catheter apparatus 20 may then be advanced over the guide wire 22 from the proximal end thereof carrying the stent 11 therewith to be positioned at the stenosis site. Once so positioned, the balloon 32 may be inflated by inflation fluid passed through the cavity 28, pressurizing the interior of the balloon to expand it by force radially outwardly into the light fibers 45, whereby the light fibers 45 transfer the expansion force to the stent 11 to distend to its fully expanded position. An external light source transmissibly connected to the light fibers will then be energized to project light through the respective fibers to the diagonally cut distal ends 46 acting as radial illuminators to direct light radially outwardly toward the inner wall 14 of the stent, for transmission through such wall to illuminate the resin 19. Illumination of the resin will initiate curing thereof causing it to take an initial set tending to maintain the full extended diameter as established by balloon inflation.

Meanwhile, the porous inner and outer walls 14 and 16 of the stent will act to pass therethrough molecules of moisture from the patient's lumen thus further accelerating the cure rate of the moisture curable resin 19 to thereby cause it to take a relatively rapid rigidized configuration assuming the maximum diameter established by inflation of the balloon. After a set period of time, the balloon 32 will be deflated and the catheter apparatus retracted and removed.

The dimensions of the intravascular catheter will generally follow the dimensions of intravascular catheters used in angioplasty procedures in the same arterial location. Typically, the length of a catheter for use in the coronary arteries is about 150 cm, the outer diameter of the catheter shaft is about 0.035 inch (0.89 mm), the length of the balloon is typically about 2 cm and the inflated diameter about 1 to about 8 mm. Should a light fiber array be placed about the balloon, the array may add some radial thickness to the distal assembly. Expandable stents, like the present invention, have an uncompressed outer diameter of about 0.06 inch in the unexpanded condition, and can be expanded to an outer diameter of 0.1 inch-or more. Typical wall thickness of an expandable stent is about 0.003 inch. The thickness of a stent wall with encapsulated resin may be somewhat greater.

The present invention has been described herein in terms of a stent with light curable and water curable resin contained in the stent wall, the stent wall formed to transmit light from at least one side and to admit water from at least one side, and a catheter system for delivering, expanding, rigidizing, and inserting in vivo an expandable stent containing light curable resin in the encapsulated stent wall. Various changes and improvements may also be made to the invention without departing from the scope thereof.

What is claimed:

1. A stent for implanting in a body lumen, comprising:
   a tubular wall defining a flexible stent body compressible to a delivery configuration and expandable to an implanted configuration;
   the wall being formed with at least one chamber;
   a resin deposited in the chamber, the resin being responsive to light and fluid to cure to assume a rigid condition;
   the wall including at least one transmissive section formed to provide for transmission of light from the exterior of the wall to the resin;
   the wall including at least one porous section to provide for transmission of fluid to the resin.

2. The stent of claim 1 for use with an expandable member wherein the stent body is configured with a passage to receive the expandable member in the compressed configuration and to expand in expansion relationship with the expandable member to the implanted configuration.

3. The stent of claim 1, wherein the chamber is formed with a discreet pocket at a selected spot and the resin is disposed in the pocket to, when cured, provide support at the selected spot.

4. The stent of claim 1, wherein the stent body is constructed of biocompatable polymer.

5. The stent of claim 1, whine the resin is radiopaque.

6. The stent of claim 1, wherein the wall is elastic.

7. The stent of claim 1, wherein the wall is biodegradable.

\* \* \* \* \*